United States Patent
Richards

(10) Patent No.: US 9,756,832 B2
(45) Date of Patent: Sep. 12, 2017

(54) DEVICE AND METHOD FOR ADMINISTERING ORAL DISINFECTING SOLUTIONS AND OTHER MEDICAMENTS

(75) Inventor: James C. Richards, Sudbury, MA (US)

(73) Assignee: Assure Pet Health, Inc., Sudbury, MA (US)

( * ) Notice: Subject to any disclaimer, the term of this patent is extended or adjusted under 35 U.S.C. 154(b) by 805 days.

(21) Appl. No.: 13/983,072

(22) PCT Filed: Feb. 1, 2012

(86) PCT No.: PCT/US2012/023462
§ 371 (c)(1),
(2), (4) Date: Aug. 1, 2013

(87) PCT Pub. No.: WO2012/118592
PCT Pub. Date: Sep. 7, 2012

(65) Prior Publication Data
US 2013/0298839 A1    Nov. 14, 2013

Related U.S. Application Data

(63) Continuation of application No. 13/018,955, filed on Feb. 1, 2011, now Pat. No. 8,470,303.
(Continued)

(51) Int. Cl.
*A01K 7/00*    (2006.01)
*A01K 7/02*    (2006.01)
(Continued)

(52) U.S. Cl.
CPC ............... *A01K 7/02* (2013.01); *A01K 7/06* (2013.01); *A01N 59/12* (2013.01); *A61K 8/20* (2013.01);
(Continued)

(58) Field of Classification Search
CPC ... A01K 7/02; A01K 8/20; A01K 7/06; A61K 33/18; A61K 8/20; C02F 2103/20;
(Continued)

(56) References Cited

U.S. PATENT DOCUMENTS 3,973,519 A * 8/1976 McCarty ............... A01K 63/04
119/227
4,000,742 A * 1/1977 Digicomo ............... E03D 9/085
4/420.1
(Continued)

*Primary Examiner* — Joshua J Michener
*Assistant Examiner* — Devin Barnett
(74) *Attorney, Agent, or Firm* — Anthony Janiuk; Clifford H. Kraft

(57) ABSTRACT

Embodiments of the present invention feature devices and methods for administering medicaments to subjects and, in particular, molecular iodine to animals in drinking water for the treatment of oral bad breath and disease. An exemplary device comprises a source of medicament in a fluid, measuring means, an administration switch and a water reservoir means. The measuring means is in fluid communication with said source of medicament for measuring an aliquot of medicament corresponding to a dose for the treatment of a disease. The measuring means is also in communication with a water reservoir means and releases the aliquot into the water reservoir means upon signal activation. The administration switch means is in signal communication with the measuring means and upon activation by a subject produces an activation signal received by the measuring means. The water reservoir means is for receiving the aliquot and forming an aqueous solution of medicament.

12 Claims, 3 Drawing Sheets

Related U.S. Application Data

(60) Provisional application No. 61/300,630, filed on Feb. 2, 2010.

(51) Int. Cl.

| | | |
|---|---|---|
| *A01N 59/12* | (2006.01) | |
| *A61K 8/20* | (2006.01) | |
| *A61Q 11/00* | (2006.01) | |
| *C02F 1/00* | (2006.01) | |
| *C02F 1/76* | (2006.01) | |
| *A01K 7/06* | (2006.01) | |
| *A61K 33/18* | (2006.01) | |
| *C02F 1/68* | (2006.01) | |
| *C02F 103/20* | (2006.01) | |
| *C02F 1/28* | (2006.01) | |
| *C02F 1/42* | (2006.01) | |
| *C02F 103/02* | (2006.01) | |

(52) U.S. Cl.
CPC ............. *A61K 33/18* (2013.01); *A61Q 11/00* (2013.01); *C02F 1/003* (2013.01); *C02F 1/008* (2013.01); *C02F 1/686* (2013.01); *C02F 1/766* (2013.01); *C02F 1/283* (2013.01); *C02F 2001/427* (2013.01); *C02F 2103/026* (2013.01); *C02F 2103/20* (2013.01); *C02F 2303/185* (2013.01); *C02F 2307/10* (2013.01)

(58) Field of Classification Search
CPC .......... C02F 1/766; C02F 1/008; C02F 1/003; C02F 1/283; C02F 1/686; C02F 2001/427; C02F 2103/026; C02F 2303/185; C02F 2307/10; A61Q 11/00; A01N 59/12
USPC ... 211/51.01, 51.02, 51.11, 51.5, 72, 74, 75; 119/51.01, 51.02, 51.11, 51.5, 72, 74, 75
See application file for complete search history.

(56) References Cited

U.S. PATENT DOCUMENTS

| | | | | |
|---|---|---|---|---|
| 4,463,706 A * | 8/1984 | Meister | ............... | A01K 7/02 119/51.02 |
| 4,617,876 A * | 10/1986 | Hayes | ............... | A01K 1/0023 119/51.02 |
| 4,986,221 A * | 1/1991 | Shaw | ............... | A01K 7/02 119/73 |
| 5,813,363 A * | 9/1998 | Snelling | ............... | A01K 7/027 119/73 |
| 5,919,374 A * | 7/1999 | Harvey | ............... | C02F 1/50 210/742 |
| 6,463,880 B1 * | 10/2002 | Callingham | ............... | A01K 7/00 119/73 |
| 6,497,197 B1 * | 12/2002 | Huisma | ............... | A01K 5/02 119/75 |
| 6,928,954 B2 * | 8/2005 | Krishnamurthy | ............... | A01K 7/025 119/51.5 |
| 7,107,931 B1 * | 9/2006 | Forster | ............... | A01K 9/00 119/51.11 |
| 7,152,550 B2 * | 12/2006 | Walker | ............... | A01K 5/0291 119/51.11 |
| 7,281,494 B1 * | 10/2007 | Connerley | ............... | A01K 7/02 119/74 |
| 7,762,211 B1 * | 7/2010 | McDaniel | ............... | A01K 5/0291 119/51.5 |
| 7,954,457 B2 * | 6/2011 | Trompen | ............... | A01K 11/001 119/655 |
| 8,104,431 B2 * | 1/2012 | Klenotiz | ............... | A01K 7/04 119/72 |
| 8,651,056 B2 * | 2/2014 | Gass | ............... | A01K 7/027 119/72 |
| 9,151,023 B2 * | 10/2015 | Taylor | ............... | E03B 7/08 |
| 2002/0134313 A1 * | 9/2002 | Andrew King | ............... | A01K 5/025 119/51.02 |
| 2003/0049352 A1 * | 3/2003 | Mehansho | ............... | A23L 1/302 426/66 |
| 2006/0288947 A1 * | 12/2006 | Perlsweig | ............... | A01K 7/022 119/75 |
| 2007/0017453 A1 * | 1/2007 | Fritter | ............... | A01K 1/0154 119/173 |
| 2007/0071693 A1 * | 3/2007 | Kurihara | ............... | A61K 38/185 424/50 |
| 2008/0190374 A1 * | 8/2008 | Farris | ............... | A01K 7/00 119/74 |
| 2010/0301640 A1 * | 12/2010 | Heiser | ............... | A47C 1/06 297/135 |
| 2011/0195033 A1 * | 8/2011 | Richards | ............... | A01N 59/12 424/51 |
| 2012/0017839 A1 * | 1/2012 | Veness | ............... | A01K 7/00 119/74 |
| 2013/0276716 A1 * | 10/2013 | Nisbet | ............... | A01K 1/0052 119/409 |
| 2015/0160171 A1 * | 6/2015 | Anzellotti | ............... | G01N 30/74 73/61.48 |
| 2015/0208609 A1 * | 7/2015 | Tillet | ............... | A01K 7/02 119/74 |
| 2015/0230438 A1 * | 8/2015 | Barber | ............... | A01K 63/045 119/259 |
| 2015/0264897 A1 * | 9/2015 | Limcaco | ............... | A01K 63/04 119/224 |
| 2015/0296744 A1 * | 10/2015 | Chumbley | ............... | A01K 7/04 119/73 |
| 2016/0007565 A1 * | 1/2016 | Trottier | ............... | A01K 5/02 119/51.02 |

* cited by examiner

DEVICE AND METHOD FOR ADMINISTERING ORAL DISINFECTING SOLUTIONS AND OTHER MEDICAMENTS

RELATED APPLICATIONS

This application is a National Phase Application of PCT International Application No. PCT/US2012/23462, International Filing Date Feb. 1, 2012, which claims priority to U.S. Provisional Patent Application No. 61/300,630, filed Feb. 2, 2010, and U.S. Non-Provisional patent application Ser. No. 13/018,955, filed Feb. 1, 2011, which applications are incorporated herein by reference.

FIELD OF THE INVENTION

Embodiments of the present invention are directed to devices and methods for administering oral disinfecting solutions and other medicaments. Embodiments of the present invention are particularly suited for treating oral disease in animals and humans and feature the use or molecular iodine.

BACKGROUND OF THE INVENTION

In order to facilitate an understanding of the present invention, this application will use the following terms as defined below.

As used herein, the term "bad oral breath" is used to mean a condition of an animal or human in which the breath carries a foul odor. This odor is caused by microbes in the mouth between the teeth and gum tissue and may take on a "rotten egg" smell due to the production of sulfur containing disease. Infection of the area between the teeth and gums is referred to as periodontal disease.

Iodine exists in many forms in aqueous solution at room temperature and neutral pH. These forms include $I^-$, $I_2$, HOI, $H_2OI^+$, $OI^-$, $I_3^-$, and $I_5^-$. The term "molecular iodine" is used to denote the $I_2$ form of iodine.

There is a need to treat or prevent bad oral breath and/or periodontal disease in animals and humans.

SUMMARY OF THE INVENTION

Embodiments of the present invention feature devices and methods for administering a medicament to an animal or human. The medicaments are useful for the treatment of active disease or to prevent the occurrence of disease. The term "treat" or "treatment" is used herein to encompass both the treatment of active disease and the prevention of disease. One embodiment of the present invention is directed to a device for administering a medicament for the treatment of a disease. The device comprises a source of medicament in a fluid, measuring means, an administration switch and a water reservoir means. The measuring means is in fluid communication with said source of medicament for measuring an aliquot of medicament corresponding to a dose for the treatment of a disease. The measuring means is also in communication with a water reservoir means and releases the aliquot into the water reservoir means upon signal activation. The administration switch means is in signal communication with the measuring means and upon activation by a subject, such as a human or animal, produces an activation signal received by the measuring means. The water reservoir means is for receiving the aliquot and forming an aqueous solution of medicament.

As used herein the term "medicament" is a drug, pharmaceutical, nutraceutical, vitamin, antimicrobial, dietary supplement, or disinfectant. One antimicrobial is molecular iodine. Molecular iodine may also be used as a dietary supplement for thyroid function. Molecular iodine in an aqueous solution is well suited for the disinfection of the oral cavity. One source of medicament comprises a vessel containing molecular iodine in an ethanol solution. One embodiment of the present invention features molecular iodine added to the water reservoir means as an absolute alcohol solution saturated with $I_2$. An effective amount of this solution is formed with 1.0 to 0.001 ml, more preferably, 0.1 to 0.025 ml, to about 0.05 ml. This effective amount in about 250 to about 800 ml of water forms, if consumed by the animal is no more than about 250 to 1500 micrograms of iodine per day, an amount that is safe and effective for thyroid function.

Embodiments of the present invention feature several sources of medicament. These sources may take the form of tanks, conduits and pumps. One embodiment features a tank, an integral vessel that receives external fluid containing medicaments. Another embodiment features a vessel as a replaceable consumable which is fitted to, or constructed and arranged to cooperate with conduits and/or pumps to communicate with, measuring means. One embodiment of the present invention comprises a tank or vessel which is pressurized to propel liquid medicament. Although reference is made to pumps or pressurized vessels, the fluid may move from the source of medicament to the measuring means by gravity feed without pressure and without pumps.

Embodiments of the present invention feature measuring means such as a valve, a measuring vessel, a timed pump, metering syringe, and other apparatus for metering an aliquot of medicament. As used herein, the term "aliquot" is a predetermined, desired amount of liquid. The term "signal activation" is used in a mechanical, photometric and electromagnetic sense. The term comprises mechanical linkages which compel a measuring vessel, valve, timed pump, metering syringe to dispense an aliquot of medicament. In a photometric and/or electromagnetic sense, the term comprises wired, or wireless communication including WIFI, radio transmission, magnetic sensors and infrared devices which power or turn on pumps and valves and the like.

Embodiments of the present invention feature administrative switch means comprising an on/off switch for an electrical circuit which operates measuring means, a mechanical link which operates a valve, measuring vessel, timed pump, metering syringe; or a photometric or electromagnetic sensor which detect the presence of the subject. The photometric or electromagnetic sensor is in signal communication with supporting control means to activate a valve, measuring vessel, metering syringe, timed pump or the like. Supporting control means is used in the sense of analog and digital equipment which receives signals from the sensor and in response to the signal issues an activation signal to measuring means. One embodiment of the present invention features control means that detects subjects or animals. The sensors may detect the subject directly through optical or visual cues or detect a subject through tags or markers affixed to or associated with the subject. One embodiment of the present invention features a tag featuring an optical code, such as a bar code, which is sensed by administration switch means which comprises an optical scanner. One embodiment comprises a tag having a radio or optical coding device, for example, a RFID device, which is detected by a sensor. Tags and sensors which can detect a subject from a population of potential subjects are used in embodiments of the present invention to denote an identified subject or identified animal. Different tags having different codes are used to denote one of more identified animals from the potential population or separate identified animals for different medicaments or doses.

Embodiments of the present invention feature administrative switching means having control means in the form of computer processing units (CPUs) integrated into a device comprising the measuring means as well as computers, servers, personal computers, internet linked computers and the like, in signal communication with measuring means but not integral therewith. Embodiments of the present invention feature control means having memory to store information regarding selected subjects and the administration of medicaments. Embodiments further comprise timing elements or clock functions and programming to administer medicament in accordance with a schedule. For example, molecular iodine is administered to a selected subject or animal once or twice daily or more times daily.

As used herein the term "water reservoir means" comprises a space constructed and arranged to receive a sized or shaped fluid receptacle, a fluid receptacle integral with the device or a disposable or removable cup, feeding and/or watering bowl or glass.

A further embodiment of the present invention further comprises purge means in communication with the water reservoir. Purge means removes medicament from the water reservoir. One embodiment of the invention features purge means in the form of a waste reservoir or adsorption materials such as filters and activated charcoal. Purge means can be constant or switched by a purge switch which directs the liquids in the water reservoir means to adsorption materials or into the waste reservoir. That is, the purge means is in signal communication with a purge switch means and is actuated by a purge signal. The purged switch means comprises a timed electrical or timed mechanical switch that is coordinated with the administration switch means, or a separate or combined with administration switch means, including incorporation of programming in control means such as a CPU. For example, without limitation, one control means is programmed issue a purge signal after an animal leaves the water reservoir.

A further embodiment of the present invention is directed to a method for administering a medicament to an animal. The method comprising the steps of providing a device having a source of medicament in a fluid, measuring means, an administration switch, and water reservoir means as previously described. Embodiments of the present method are well suited for the administration of molecular iodine to the oral cavity of a subject such as a human or an animal.

These and other features and advantages will be apparent to those skilled in the art upon viewing the drawings and reading the detailed description that follows.

DETAILED DESCRIPTION OF THE INVENTION

Embodiments of the present invention feature devices and methods for administering a medicament to an animal or human. These embodiments will be described in detail as a device and method for administering molecular iodine to an animal, such as a dog, for the treatment of bad oral breath and preventing plaque formation. Those skilled in the art will recognize that embodiments of the present invention have application for the treatment of human disease and other animal and other diseases. The embodiments described are the best mode of the invention as presently contemplated. However, embodiments of the present invention can be modified and altered and the descriptions herein should not be considered limiting.

Figure 1:
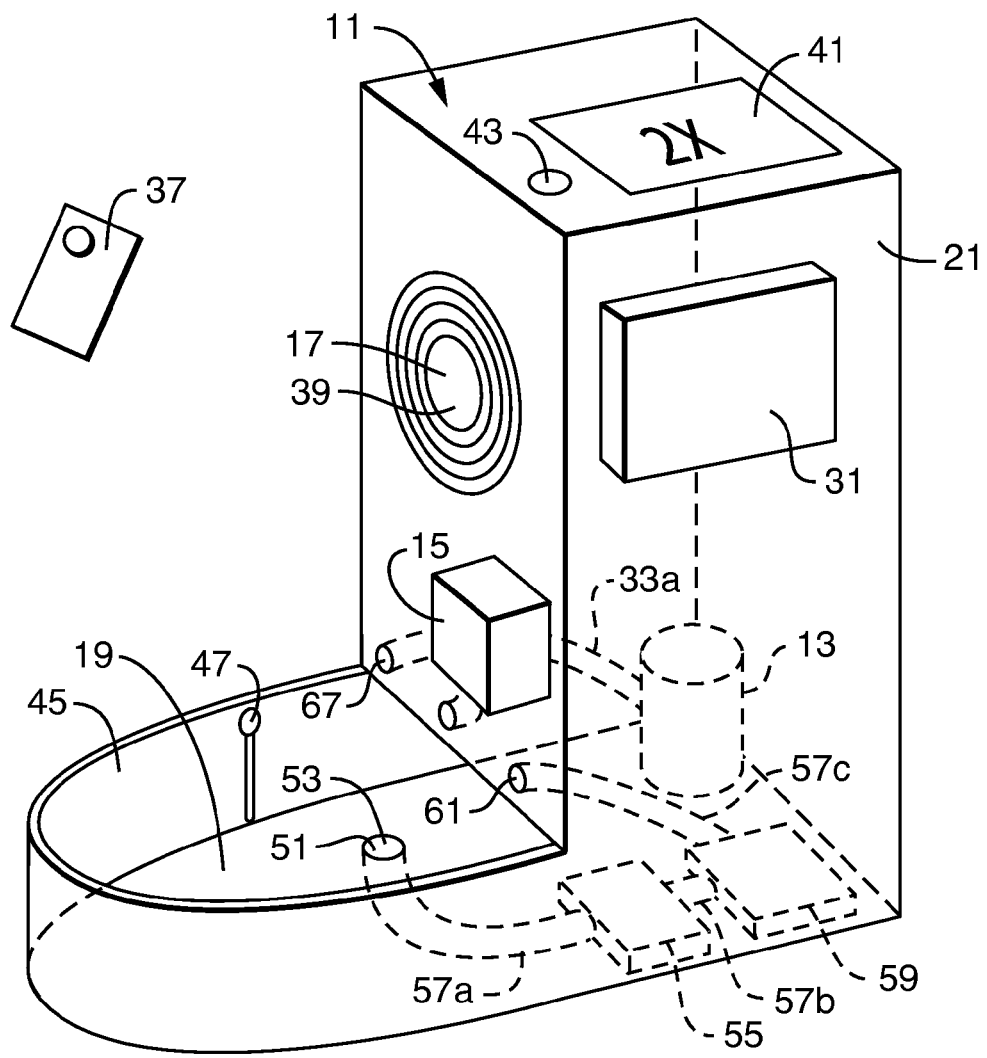
FIG. 1 depicts a device embodying features of the present invention.

Turning now to FIG. 1, a device, embodying features of the present invention, is designated with the numeral 11. The device 11 is for administering a medicament, molecular iodine, for the prevention or treatment of a disease, bad oral breath in a dog [not shown in FIG. 1]. The device 11 comprises a source of medicament in a fluid 13, measuring means 15, an administration switch 17 and a water reservoir means 19, held in a housing 21.

The source of medicament 13 comprises a vessel containing molecular iodine in an ethanol solution. The molecular iodine is added to the water reservoir means 19 as an absolute alcohol solution saturated with $I_2$. An effective amount of this solution is formed with 1.0 to 0.001 ml, more preferably, 0.1 to 0.025 ml, to about 0.05 ml. This effective amount in about 500 ml of water forms, if consumed by the animal is no more than about 250 to 500 micrograms of iodine daily, an amount that is safe and effective for thyroid function and an amount that substantially disinfects the oral cavity of an animal.

Sources of medicament 13 may take several forms, such as without limitation, tanks, conduits, pumps, bags, pouches, cartridges, vials, bottles, syringes and pressurized cans. Embodiments featuring a tank may incorporate the tank as an integral vessel that receives external fluid containing medicaments. Or, a vessel can be a replaceable consumable which is fitted to, or constructed and arranged to cooperate with conduits and/or pumps to communicate with measuring means. Pressurized cans and containers may not need pumps and use compressed air to propel the medicament. Although reference is made to pumps or pressurized vessels, the fluid may move from the source of medicament 13 to the measuring means 15 by gravity feed without pressure and without pumps. For the purpose of this description, the source of medicament is a glass vessel containing ethanol saturated with molecular iodine.

The measuring means 15 is in fluid communication with the source of medicament 13 for measuring an aliquot of medicament corresponding to a dose for the prevention of plaque or treatment of a disease. As used herein, the term in "fluid communication" means plumbed together, or receiving fluid from one to the other. The measuring means 15 is also in communication with a water reservoir means and releases the aliquot into the water reservoir means 19 upon signal activation. The measuring means 15 comprises a timed or measured valve or pump, or metering syringe, or emptying a measuring vessel. For example, without limitation, where the medicament is held in a pressurized can, the measuring means may take the form of a dispensing valve [not shown] known in the art of the type used for dispensing aerosols and fluids. See for example: *Remington: The Science and Practice of Pharmacy*, 20$^{th}$ Edition. Lippincott Williams and Wilkins (2000) at 976-978. As depicted and described herein, the measuring means is a timed pump plumbed to the source of medicament 13 via medicament conduit 33a.

The administration switch means 17 is in signal communication with the measuring means 15. Upon activation by a subject, such as a human or animal, administration switch means 17 produces an activation signal received by the measuring means 15.

Figure 2:
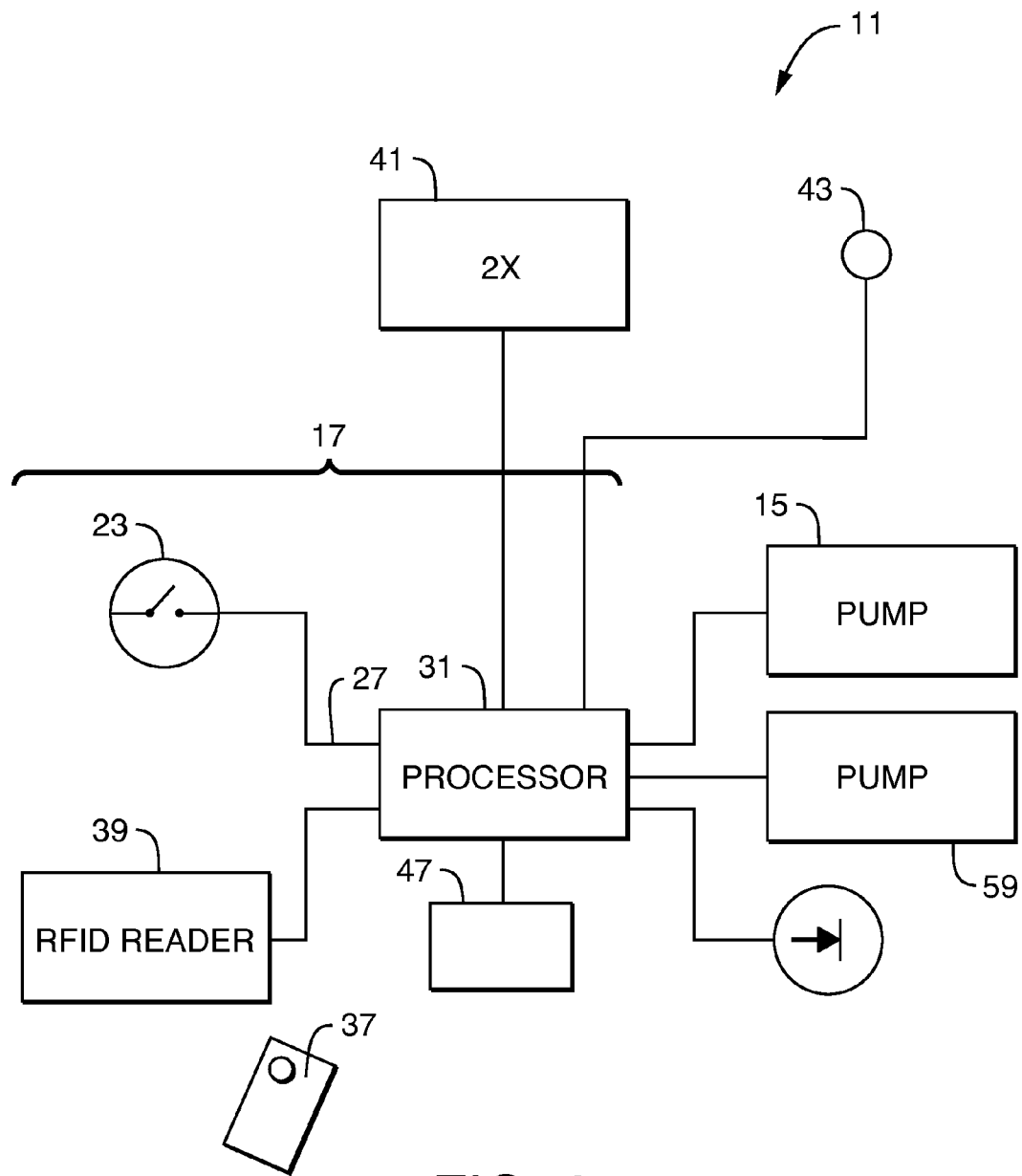
FIG. 2 depicts a schematic drawing having features of the present invention; and, FIG. 3 depicts a schematic drawing having features of the present invention.

As best seen in FIG. 2 which depicts signal communication of device 11, administration switch means 17 has an on/off switch 23 for an electrical circuit 25 which operates measuring means 17 in the form of a pump [not shown] and a purge means 51 to be described more fully below. In the alternative, the administration switch means operates a motor or solenoid [not shown] with a mechanical link to a valve, measuring vessel, timed pump, metering syringe [not shown]. The switch 23 is further in signal communication with a CPU 31 which has timing functions and scheduling programming. The timing function times the power to the pump or solenoid such that the pump, valve, measuring vessel or metered syringe dispenses a desired dose of medicament in the water reservoir means 19. The scheduling function will dispense medicament at selected times of the day and for individual subjects from a population of potential subjects.

The administration switch means 17 of FIG. 1 and FIG. 2 further comprises a photometric or electromagnetic sensor which detects the presence of the subject. For example, without limitation, one embodiment of the present invention comprises a camera [not shown] and CPU, such as CPU 31, with visual recognition software for detecting the presence of an animal. As illustrated in FIGS. 1 and 2, the photometric or electromagnetic sensor detects the presence of a tag 37. The tag 37 is recognized by sensor 39 by virtue of bar coding or other optical or electromagnetic coding. For example, one embodiment of the present invention features a sensor such as an optical scanner.

One embodiment, as illustrated, is an RFID tag 37. RFID tags are available from numerous vendors. A plurality of RFID tags 37, each coded separately for a plurality of individual subjects, are used to administer medicaments to selected or identified subjects from a population of potential subjects, at selected times or to receive selected medicaments. Tags and sensors which can detect a subject from a population of potential subjects are used in embodiments of the present invention to denote an identified subject or identified animal. Different tags having different codes are used to denote one of more identified animals from the potential population or separate identified animals for different medicaments or doses.

Although a CPU 31 is depicted in FIG. 2, control means can comprise other analog and digital equipment which receives signals from the sensor and in response to the signal issues an activation signal to measuring means 15. Embodiments of the present invention feature administrative switching means 17 having control means in the form of computer processing units (CPUs) integrated into a device 11. However, CPU 31 may be located apart from the device 11, as a separate computers, server, personal computers, internet linked computers and the like, in signal communication with measuring means 15 by means of wired or wireless communication devices.

Embodiments of the present invention feature control means such as CPU 31 having memory to store information regarding selected subjects and the administration of medicaments. Such memory is known in the art and is not shown for purposes of clarity.

Embodiments further comprise timing elements or clock functions and programming to administer medicament in accordance with a schedule. Clock functions are common in CPU systems supporting CPU 31. Scheduling programming is also well known in the art. One embodiment of the present invention features molecular iodine administered to a selected subject or animal a schedule of once or twice daily. The doses are separated in time, for example eight to twelve hours. Programming is facilitated with a display screen 41 and controls 43 as best seen in FIG. 1.

The water reservoir means 19 is for receiving the aliquot and forming an aqueous solution of medicament. Water reservoir means 19 comprises a space constructed and arranged to receive a sized or shaped fluid receptacle, a fluid receptacle integral with the device or a disposable or removable cup, feeding and/or watering bowl or glass. As best seen in FIG. 1, the water reservoir means, as depicted, is integral with the device 19 and comprises a basin 45 for holding a suitable amount of water, for example 100 to 800 ml. Water reservoir means 19 has a volume sensor 47 that detects when the basin 45 is at capacity or empty. The volume sensor 47 is in signal communication with CPU 31 which coordinates the administration switch means 17 and measuring means 15 such that medicament is not added to the basin 45 when basin 45 can not accommodate additional fluid or when the addition of medicament would not lead to an appropriate dilution.

Figure 3:
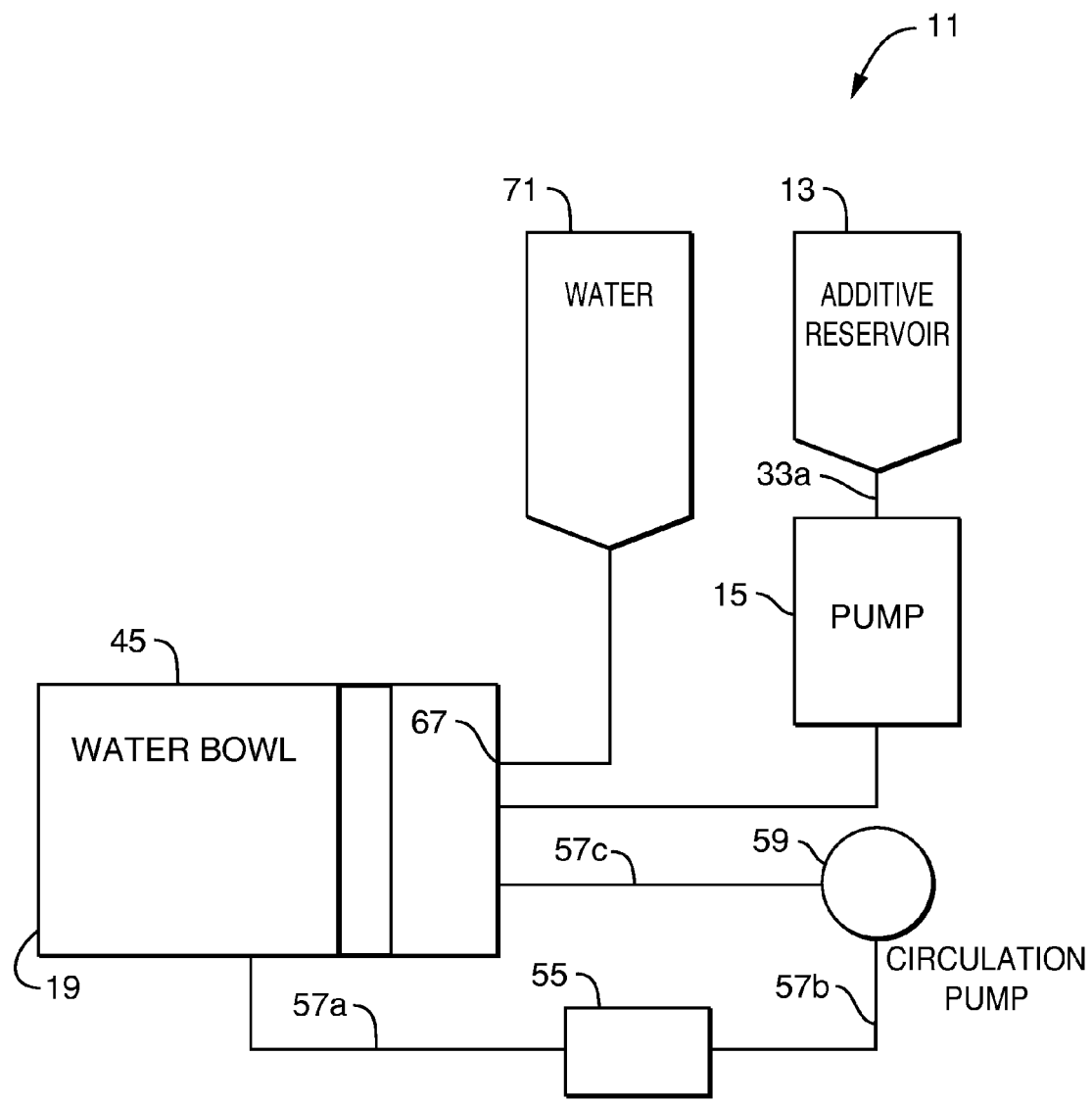

Water reservoir means 19 is in fluid communication with a source of water 71, best seen in FIG. 3 which depicts a fluid diagram of device 11. The flow of which is controlled by a valve or siphon mechanism [not shown] known in the art and under signal control of the volume sensor 47 and CPU 31 or under hydrodynamic-mechanical control. Water flows into basin 45 via water inlet 67.

As depicted in FIG. 1, the device 11 further comprises purge means 51 in communication with the water reservoir means 19. Purge means 51 removes medicament from the basin 45. As depicted, purge means 51 comprises a drain 53, purge filter 55, purge conduits 57*a-c*, pump 59 and purge outlet 61. Liquid is removed from the basin 45 through drain 53 and conveyed by purge conduits 57*a-c* to a purge filter 55, purge pump 59 and on to the purge outlet 61. Thus, water is cleaned and medicament removed and reintroduced into the basin 45.

Purge filter 55 is made of porous materials to remove hair, dust and dirt. Purge filter 55 has an activated charcoal bed to remove medicament. Removal of medicament may be advantageous where the device 11 is used in the presence of small children.

Purge means 51 may also comprise waste receptacles [not shown] for storing a volume of water. Removal of the water may obviate the need for a purge filter 55. Purge means 51 can be constant or switched by a purge switch [not shown] which directs the liquids in the water reservoir means to adsorption materials or into the waste reservoir. For example, the purge pump 59 of purge means 51 is in signal communication with a purge switch means [not shown] and is actuated by a purge signal. The purge switch means comprises a timed electrical or timed mechanical switch that is coordinated with the administration switch means 17, or separate or combined with administration switch means 17, including incorporation of programming in control means such as a CPU 31. For example, without limitation, one control means is programmed to issue a purge signal after an animal leaves the water reservoir.

The present device 11 is plumbed with a source of water 71 shown in FIG. 3 which communicates with the basin 45 through a water inlet 67. Water inlet 67 releases water to fill basin 45 under the control of water level sensor 47 and CPU 31 or mechanical hydrodynamic means [not shown] known in the art.

Embodiments of the present invention directed to a method for administering a medicament to an animal will be described in detail with respect to FIG. 1 and device 11. The method comprising the steps of providing a device 11 having a source of medicament in a fluid 13, measuring means 15, an administration switch 17, and water reservoir means 19 as previously described. A subject, such as a house pet, is fitted with a tag 37. As the subject approaches the water reservoir means 19, the tag 37 is recognized by administration switch means 17 and measuring means 15 is activated with an administration signal to dispense a dose of medicament such as molecular iodine. Administration switch means 17 recognizes the time the subject leaves the water reservoir means 19, and CPU 31 issues a purge signal to purge means 51 to remove medicament form the water reservoir means 19.

Embodiments of the present method are well suited for the administration of molecular iodine to the oral cavity of a subject such as a human or an animal. One medicament is a saturated iodine in ethanol comprising iodine crystals and absolute ethanol. In the alternative a 10% solution is prepared by dissolving 1 gram of iodine crystals in 100 ml of absolute ethanol. A 1% solution is prepared from a 1:10 dilution of the 10% solution of iodine in absolute ethanol.

EXAMPLES

Two dogs and two cats were administered molecular iodine at doses ranging from 80-1400 mcg iodine per day for one day and 1-5 mcg per day for three weeks with no ill effects.

Thus, we have described embodiments of the present invention with respect to the best mode presently contemplated with the understanding that the present embodiments can be altered and modified. Therefore, the present invention should not be limited to the discussion and figures described but should encompass the subject matter of the claims that follow and their equivalents.

The invention claimed is:

1. A device for administering molecular iodine for the treatment of an oral cavity of an animal comprising:
    a source of molecular iodine in a fluid, said fluid consisting of molecular iodine in ethanol;
    a measuring means in fluid communication with said source of molecular iodine for measuring an aliquot of molecular iodine corresponding to a dose for the treatment of the oral cavity, said measuring means is in communication with a water reservoir and releases said aliquot of molecular iodine upon signal activation;
    an administration switch in signal communication with said measuring means, said administration switch upon activation by an animal producing an activation signal received by said measuring means, said administration switch comprises animal recognition means to identify an individual animal from a population of animals, said administration switch tracks the administration of molecular iodine over time for an identified animal;
    said water reservoir receives said aliquot forming an aqueous solution of molecular iodine for disinfection of an oral cavity wherein said water reservoir is a drinking container;
    a purge means in communication with said water reservoir for removing the molecular iodine from said water reservoir;
    a purge switch in signal communication with said purge means, wherein said purge means is actuated by a purge signal; and
    said administration switch and said purge switch each comprise a control means, wherein said control means is a computer processing unit programmed to produce the activation signal when said identified animal is at said water reservoir for administration of the aliquot of molecular iodine in accordance with a schedule and said control means is programmed to issue the purge signal after the corresponding animal leaves said water reservoir.

2. The device of claim 1 wherein said control means recognizes a plurality of identified animals.

3. The device of claim 1 wherein said animal recognition means is a tag recognized by said administration switch.

4. The device of claim 1 wherein said purge means is a waste reservoir in fluid communication with said water reservoir.

5. The device of claim 1 wherein said purge means comprises an adsorption means.

6. The device of claim 5 wherein said adsorption means is activated charcoal.

7. A method for administering molecular iodine for the treatment of an oral cavity of an animal comprising the steps of:
    providing a device having:
    a source of molecular iodine in a fluid, said fluid consisting of molecular iodine in ethanol;
    a measuring means in fluid communication with said source of molecular iodine, said measuring means is in communication with a water reservoir;
    an administration switch in signal communication with said measuring means, said administration switch upon activation by an animal producing an activation signal received by said measuring means, said administration switch comprises animal recognition means;
    said water reservoir receives said aliquot forming a aqueous solution of molecular iodine for disinfection of an oral cavity wherein said water reservoir is a drinking container;
    a purge means in communication with said water reservoir for removing the molecular iodine from said water reservoir;
    a purge switch in signal communication with said purge means, wherein said purge means is actuated by a purge signal; and
    said administration switch and purge switch each comprises control means, said control means is a computer processing unit programmed to produce the activation signal when said identified animal is at said water reservoir for administration of the aliquot of molecular iodine into the water reservoir in accordance with a schedule and said control means is programmed to issue the purge signal after the corresponding animal leaves said water reservoir
    identifying an individual animal from a population of animals;
    measuring an aliquot of molecular iodine corresponding to a dose for the treatment of an oral cavity;
    releasing said aliquot of molecular iodine into said water reservoir upon signal activation produced by the individual animal;
    removing the molecular iodine from said water reservoir by a purge signal after the animal leaves said water reservoir;

tracking the administration of molecular iodine over time for an identified animal.

8. The method of claim 7 wherein said animal recognition means is a tag recognized by said administration switch.

9. The method of claim 7 wherein said purge means is a waste reservoir in fluid communication with said water reservoir.

10. The method of claim 7 wherein said purge means comprises an adsorption means.

11. The method of claim 10 wherein said adsorption means is activated charcoal.

12. The method of claim 7 wherein said control means recognizes a plurality of identified animals.

* * * * *